United States Patent
Doroshow et al.

(10) Patent No.: US 9,386,995 B1
(45) Date of Patent: Jul. 12, 2016

(54) APPARATUS AND METHOD FOR GUIDING A SURGICAL DRILL DURING ORTHOPEDIC SURGERY

(71) Applicants: Jake Doroshow, New York, NY (US);
Scott Doroshow, Philadelphia, PA (US)

(72) Inventors: Jake Doroshow, New York, NY (US);
Scott Doroshow, Philadelphia, PA (US)

( * ) Notice: Subject to any disclaimer, the term of this patent is extended or adjusted under 35 U.S.C. 154(b) by 0 days.

(21) Appl. No.: 14/736,766

(22) Filed: Jun. 11, 2015

(51) Int. Cl.
| | | |
|---|---|---|
| *A61B 17/00* | (2006.01) | |
| *A61B 17/16* | (2006.01) | |
| *A61B 17/17* | (2006.01) | |
| *A61B 19/00* | (2006.01) | |

(52) U.S. Cl.
CPC ......... *A61B 17/1615* (2013.01); *A61B 17/1703* (2013.01); *A61B 17/1717* (2013.01); *A61B 19/54* (2013.01); *A61B 2019/5466* (2013.01)

(58) Field of Classification Search
None
See application file for complete search history.

(56) References Cited

U.S. PATENT DOCUMENTS

| | | | |
|---|---|---|---|
| 5,346,496 A | | 9/1994 | Pennig |
| 5,584,838 A | * | 12/1996 | Rona ................ A61B 17/1707 324/226 |
| 6,635,061 B1 | | 10/2003 | Snyder |
| 7,887,545 B2 | | 2/2011 | Fernandez et al. |
| 8,152,807 B2 | | 4/2012 | Edwards et al. |
| 8,216,237 B2 | | 7/2012 | Edwards et al. |
| 2005/0107792 A1 | | 5/2005 | Manderson |
| 2005/0107793 A1 | | 5/2005 | Manderson |
| 2013/0281884 A1 | | 10/2013 | Mullaney et al. |

OTHER PUBLICATIONS

Anastopoulos et al., "Evaluation of the Stryker S2™ IM Nail Distal Targeting Device for reduction of radiation exposure: A case series study", INJURY, International Journal of the Care of the Injured, vol. 39, pp. 1210-1215, 2008.

Diotte et al., "Radiation-Free Drill Guidance in Interlocking of Intramedullary Nails", Medical Image Computing and Computer-Assisted Intervention—MICCAI 2012, vol. 7510 of Lecture Notes in Computer Science, pp. 18-25, 2012.

* cited by examiner

*Primary Examiner* — Sameh Boles
(74) *Attorney, Agent, or Firm* — Michael B. Fein, Esq.; Eckert Seamans Cherin & Mellott, LLC (57) ABSTRACT

A method for inserting screws in holes in intramedullary (IM) nails comprising providing a surgical drill which in turn comprises a drill bit having an axis and two or more radiopaque circles on the drill, the circles having the same diameter and having planes which are parallel to each other and have an imaginary axis through them which is parallel to the axis of the drill bit, and confirming the alignment of the drill bit with the hole in the IM nail by adjusting the location and orientation of the drill to correspond to a position wherein the two or more radiopaque circles on the drill form a perfect circle in an x-ray image taken by a C-arm which has previously been aligned with a hole in the IM nail. The circles can be part of the drill and can flip out or be retracted or they can be part of a clip on device.

3 Claims, 11 Drawing Sheets

APPARATUS AND METHOD FOR GUIDING A SURGICAL DRILL DURING ORTHOPEDIC SURGERY

BACKGROUND OF THE INVENTION

The present invention relates to the field of orthopedic surgery, more specifically to methods and apparatus for inserting interlocking screws in intramedullary (IM) nails and for drilling and placing screws in other fractures or when using other implants which do not require IM nails. The method and apparatus are used with C-arm radiation apparatus which emits a beam between an emitter and a receiver at opposite ends of the "C" of the C-arm.

In the first type of surgery, IM nails are primarily used by orthopedic surgeons to fix fractures of the femur, tibia, or humerus, although they can be used to fix fractures in other bones as well. An IM nail is a cylindrical metal rod which includes hollow, open slots near the proximal end and near the distal end, and is designed to be placed down the center of the long femur or tibia bones. The slots are adapted to receive screws. During repair of femur and tibia fractures, an IM nail is first inserted through the center of the bone from the proximal end toward the distal end of the bone. The IM nail used for femur fractures has a proximal slot at an oblique angle and a proximal screw is inserted toward the head of the femur and through the proximal slot.

The IM nail has two distal slots, each aligned at 90° to the length of the nail, adapted to receive distal screws. After the proximal screw is inserted, the distal screws must be inserted by drilling through the distal portion of the femur and the distal slots of the IM nail, and inserting the distal screws.

While the proximal screw is typically placed by use of a guide which attaches to the top of the nail, a similar guide cannot be used to place the distal screws. Because of the distance a guide has to travel from the top of the nail to the bottom of the nail, small amounts of motion in the guide would lead to an inability to line up the guide properly with the distal drill holes. The nail geometry can change slightly as it is inserted due to body temperature and mechanical forces placed on it during insertion, which is another reason guides cannot be used reliably for the distal screws in this type of surgery.

Placing the distal screws close to 90° to the length of the nail is very important since it decreases the friction between the IM nail and the screw and more evenly spreads out the forces which the screw encounters, reducing the risk that the screw will break over time. Such placement also optimizes the prevention of up and down movement of the IM nail in relation to the bone and prevents the nail from rotating.

The current state of the art is to place distal screws by a freehand technique called "perfect circles" with the assistance of an X-ray machine called a C-arm (FIG. 1) which consists of two cylinders, one of which emits an x-ray beam and the other of which captures an image. The C-arm is set up next to the patient and is turned 90° with the patient's leg being placed between the two cylinders in order to get the X-ray machine and beam parallel to the ground and perpendicular to the leg (FIG. 2).

Then the patient's leg is moved manually with the goal of lining up the entry and exit holes in the nail with the x-ray beam. Then an X-ray image is taken. If the entry and exit holes are lined up perfectly, the image of the slot shows one "perfect circle." If the image shows clear overlap, the leg is readjusted and another image is taken, repeating this process until perfect circles are achieved. Then the surgeon places the tip of the drill in the exact center of the perfect circles.

While keeping the tip of the drill bit in the exact center of the perfect circles, the surgeon visually tries to align the back end of the drill with the imagined plane of the X-ray beam which goes through the leg, between the two cylinders of the C-arm. Then the surgeon drills through the bone, through the exit and entry of a hole in the IM nail. The prior observation of a perfect circle in the X-ray image of the distal IM nail hole proves that the C-arm is perfectly parallel to the hole. By manually aligning the direction of the drill bit with an imaginary line between the C-arm cylinders, the surgeon attempts to drill through the bone and the hole in the IM nail.

In the second type of surgery, a fracture is repaired by drilling a hole on an offset angle to the length of a bone, ideally situated perpendicular to the fracture line that is being fixed. The surgeon then places a screw through the previously drilled hole, ideally at 90 degrees through the line of the fracture.

The methods currently in use are not always successful, resulting, in the case of the first type, in the screw sitting obliquely or even outside the IM nail, either in front of or behind it. In the case of the second type, the surgeon is not always able to place the screw in the exact desired and optimum location, which may lead to suboptimal alignment and compression of the fracture fragments.

There have been many attempted solutions proposed by others, including complicated, sophisticated, and expensive apparatus, but none of those proposed solutions have been widely adopted by orthopedic surgeons. Thus there has been a long-felt need for a lower cost, simple, and highly effective solution to this problem.

SUMMARY OF THE INVENTION

The problems with prior art methods and systems for inserting interlocking screws in distal holes in intramedullary (IM) nails are addressed by the present invention which comprises in one aspect a method comprising of two or more radiopaque circles on the drill, perfectly aligned parallel with the drill bit, and confirming the alignment of the drill bit with the hole in the IM nail by adjusting the location and orientation of the drill to correspond to a position wherein the two or more radiopaque circles on the drill form a perfect circle in an x-ray image taken by the C-arm which has previously been aligned with a hole in the IM nail. The axis through the centers of the circles will be parallel to and a known distance above the axis of the drill bit and so when the circles appear as one circle in an x-ray, i.e., as perfect circles, the axis of the drill bit is aligned with the axis through the center of the target distal hole in the IM nail.

In some embodiments one or more x-rays are taken to confirm the drill is aligned so that the drill bit is located on the correct axis with the intended distal hole in the IM nail by assuring that the external radiopaque circles on the drill form a perfect circle in an x-ray image. In other embodiments an x-ray video image of the two or more circles is displayed on a monitor so that the surgeon can determine whether the drill bit is aligned with the intended axis.

The two or more radiopaque circles on the drill aligned with the axis of the drill bit can be above or on either side of the drill and can be removed or folded down on the drill when not needed.

In another aspect the invention comprises a surgical drill having a drill bit, the drill bit having an axis, the drill having two or more radiopaque circles each having a plane perpendicular to the axis of the drill bit, the plane of each circle parallel to the plane of each other circle, the circles located along the top side or along either side of the drill.

In one embodiment of the surgical drill, there are two circles on a member or portion which is attached to and can be removed from the top or side of the drill. In one embodiment a device comprising the two circles clips on to the top of the drill and can be removed when not needed.

In another embodiment the circles are built into the top of, or a side of the drill, and can be unfolded out when needed and folded back into the drill when not needed.

In some embodiments the two or more circles are mounted on the drill on an adjustable linkage or hinge to allow flexing, rotation, and/or extension and can be used in a surgical procedure to place a screw in a fracture which is not in line with the C-arm beam.

The circles can be plastic or metal. In the clip on device embodiments the circles and the clip on portion can be molded of plastic and designed to correspond to the shape of the surgical drill so that it may be easily and very quickly clipped on when needed. The device can also be adjustable, giving the ability to tighten or loosen, so if it is not molded to a specific drill model, it can be fastened on to many different drill styles. In other embodiments the clip on device can be made of spring metal.

In another aspect of the invention the two or more circles are mounted on the drill on an adjustable linkage or hinge to allow flexing, rotation, and/or extension and are used to place a screw in a fracture which is not in line with the C-beam.

DETAILED DESCRIPTION

Figure 1:
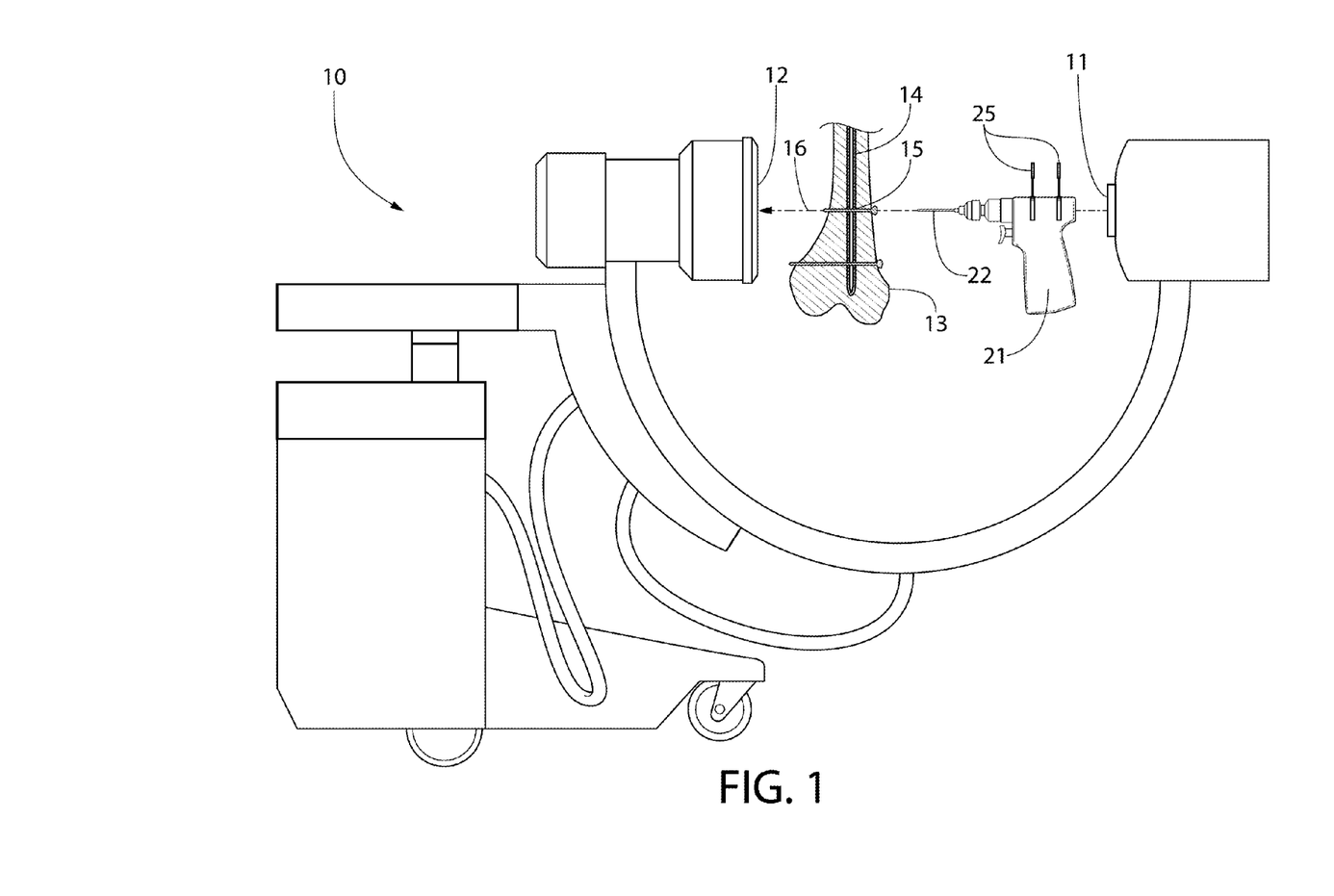
FIG. 1 is a C-arm having an imaginary axis aligned with the axis of a bit of a surgical drill, including a cross-sectional view of the distal portion of a femur having an IM nail inserted, illustrating two distal holes through the IM nail with screws properly inserted through the femur bone and through the holes.
Figures 2, 3:
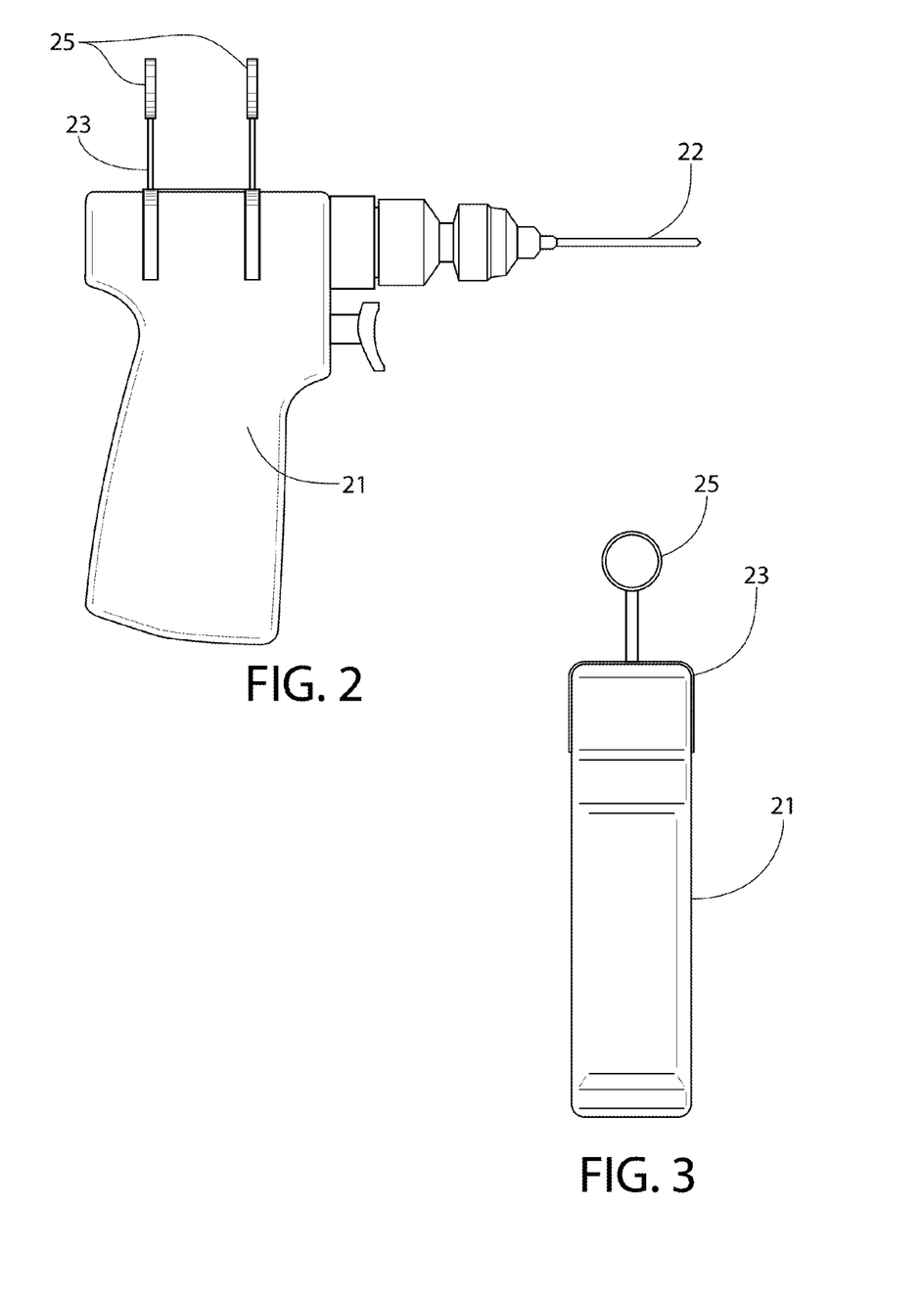
FIG. 2 is a perspective surgical drill showing clip on device of invention.
FIG. 3 is a rear perspective view of the drill of FIG. 2.

Referring first to the drawings, FIG. 1 illustrates a C-arm 10 having an emitter 11 and receiver 12, with a femur 13 illustrated within the C-arm beam 16, the femur 13 having an IM nail inserted (shown in cross section), the IM nail 14 having distal holes 15. A surgical drill 21 is aligned with the C-arm beam 16. A clip on device is shown on the drill having holes 25 aligned parallel with the drill bit.

FIG. 2 is a side view of a surgical drill 21 having a drill bit 22 and a clip on device 23 of the invention which includes radiopaque circles 25. The drill 21 is shown in FIG. 1 aligned so that the drill bit 22 is on the axis through the center of a distal hole 15, the axis being aligned with the C-arm beam 16 between the emitter 11 and receiver 12 of the C-arm 10. The circles 25 are aligned with the direction of the C-arm beam.

Figure 4:
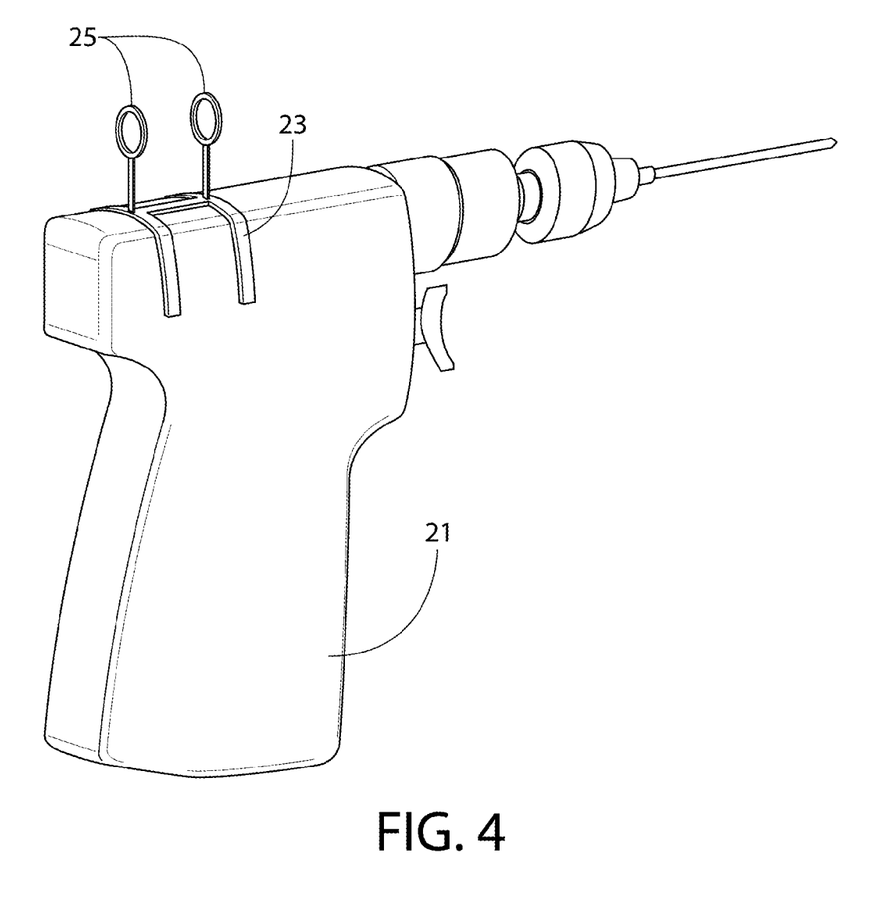
FIG. 4 is a perspective view from the side of the drill of FIG. 2, turned slightly counter-clockwise.

FIG. 3 is a rear view of FIG. 4 is a view showing the top, side, and rear of drill 21 with clip on device 23.

Figure 5:
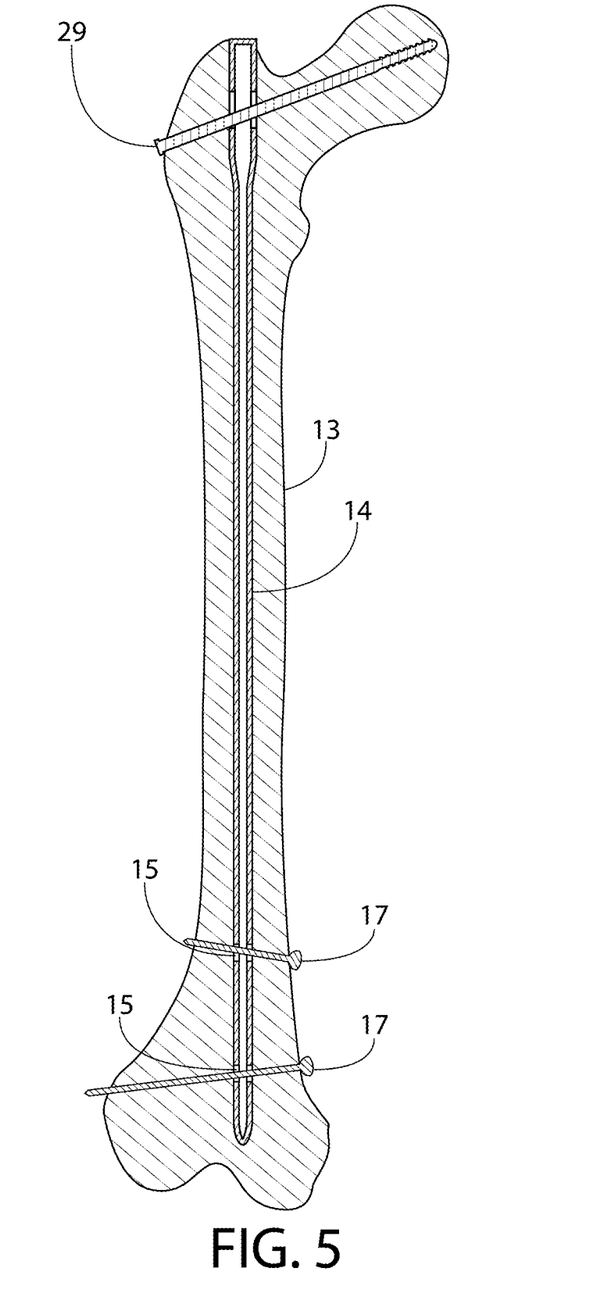
FIG. 5 is a cross-sectional view of a femur having an IM nail inserted through the femur bone, illustrating a proximal screw properly inserted through the femurand the proximal hole in the IM nail and two distal holes through the IM nail with screws improperly inserted through the femur bone and through the holes.

Shown in FIG. 5 is a cross sectional view of femur 13 with the IM nail 14 inserted, illustrating distal screws 17 improperly inserted through holes 15.

Figure 6:
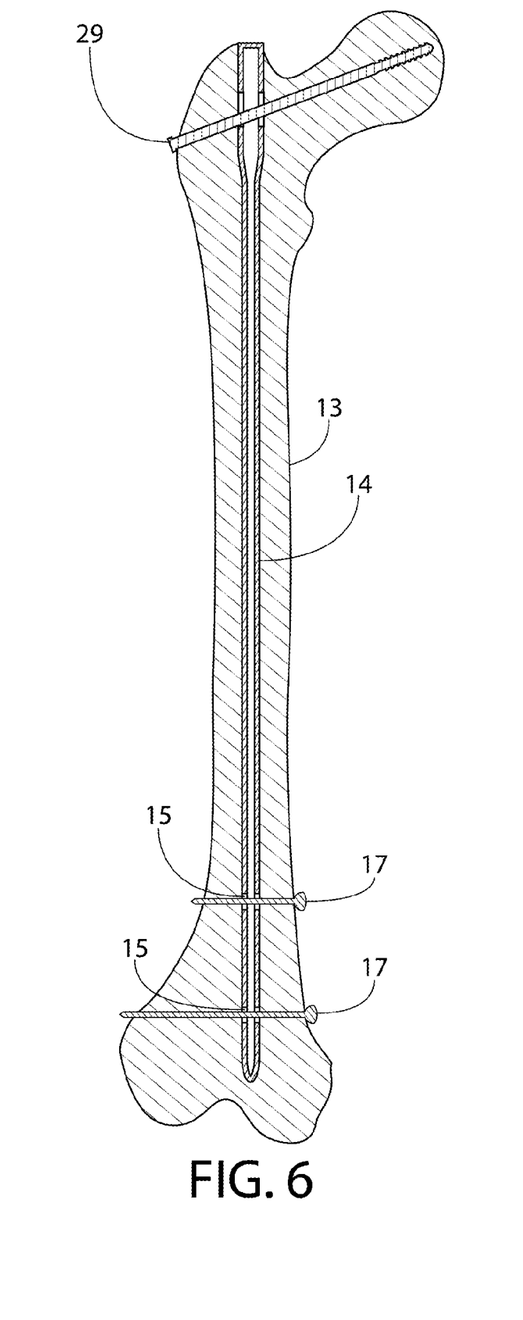
FIG. 6 is a cross-sectional view of a femur having an IM nail inserted through the femur bone, illustrating a proximal screw properly inserted through the femur and the proximal hole in the IM nail and two distal holes through the IM nail with screws properly inserted through the femur bone and through the holes.

FIG. 6 is a cross-sectional view of femur 13 with distal screws 17 properly inserted in holes 15, i.e. at a 90° angle to the length of the IM nail 14.

Figure 7:
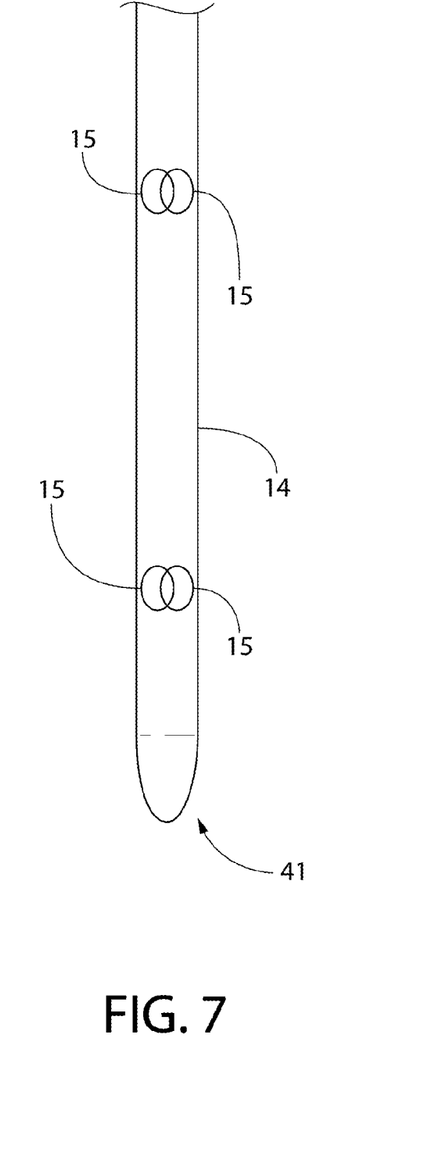
FIG. 7 is an x-ray image of an IM nail illustrating imperfect circles of two distal holes when the C-arm is improperly aligned horizontally.

FIG. 7 illustrates an X-ray image 41 of distal hole 15 when C-beam 16 is not aligned. The C-arm 10 or the patient's leg is moved so that the X-ray image 51 (FIG. 9) of distal hole 15 forms a perfect circle 42 of hole 15 when the C-arm beam 16 is aligned with the axis through the hole 15.

Figure 19:
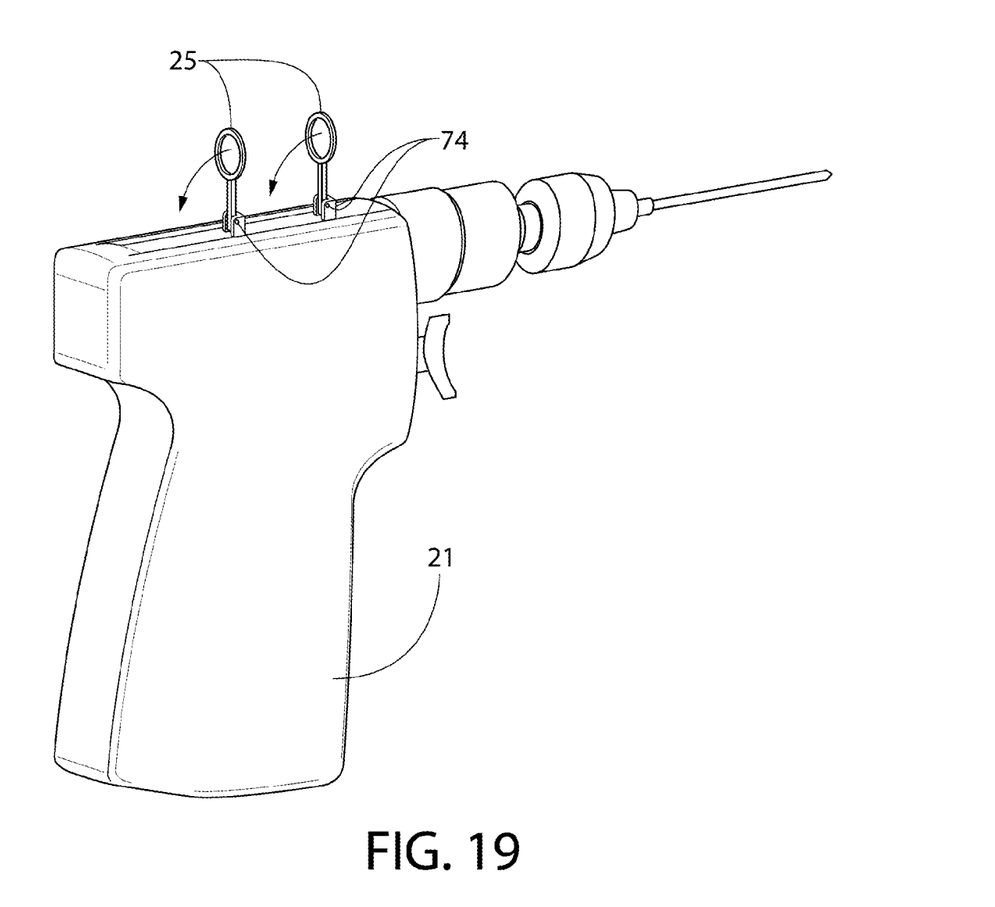
FIG. 19 is perspective view from the side of an embodiment of a drill, turned slightly counter-clockwise, wherein rather than a clip on device, circles are permanently mounted on the drill and can be flipped down when not in use.

In another embodiment of the invention, a drill 21 is shown in FIG. 19 with circles folding out from the top of the drill. In this embodiment the drill 21 has built in circles 25 which are hinged so that they can be folded out when needed or folded back in when not needed.

FIG. 7 is an x-ray image of an IM nail 14 illustrating imperfect circles 15 of two distal holes when the C-arm is improperly aligned horizontally.

Figure 8:
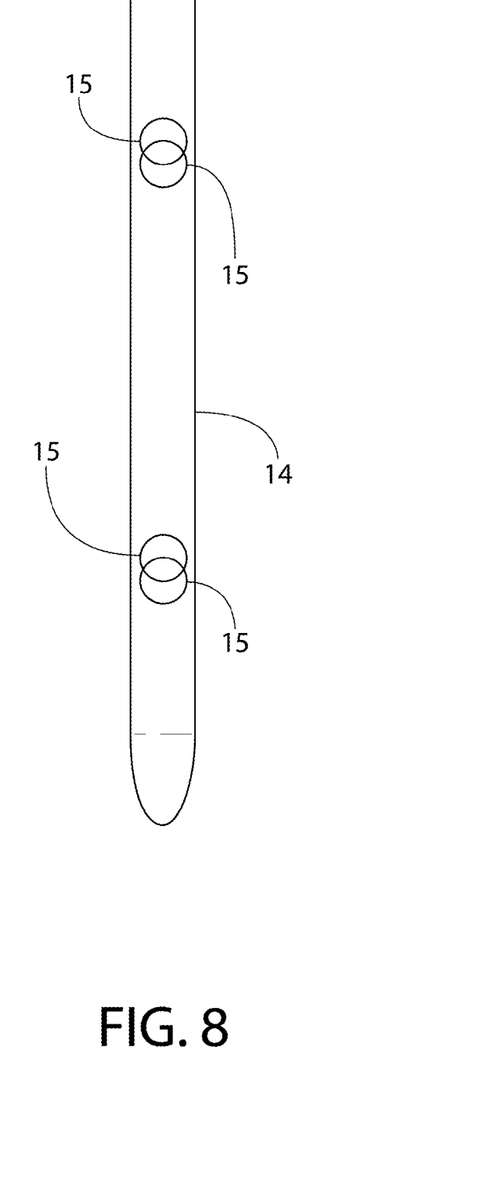
FIG. 8 is an x-ray image of an IM nail illustrating imperfect circles of two distal holes when the C-arm is improperly aligned vertically.

FIG. 8 is an x-ray image of an IM nail 14 illustrating imperfect circles 15 of two distal holes when the C-arm is improperly aligned vertically.

Figure 9:
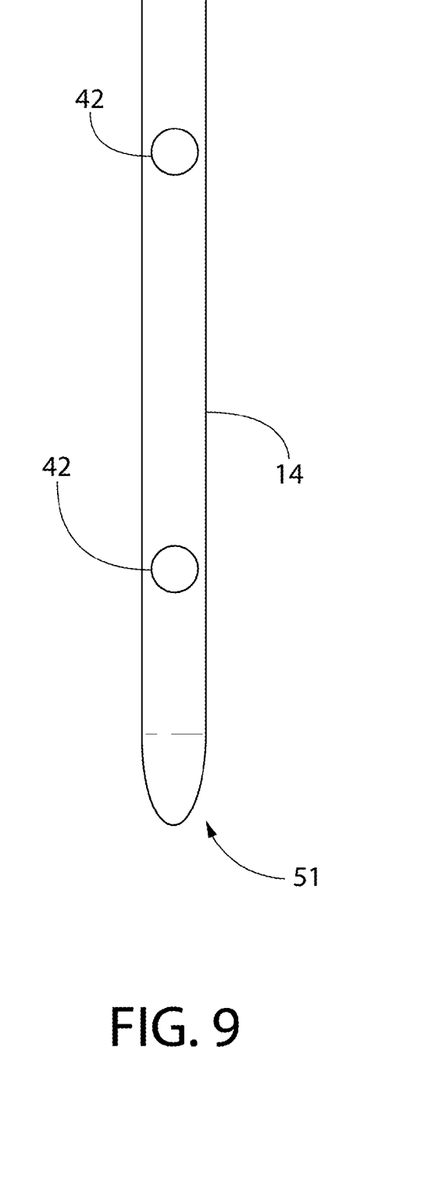
FIG. 9 is an x-ray image of an IM nail illustrating perfect circles of two distal holes when the C-arm is properly aligned along the ideal axis for insertion of distal screws.

FIG. 9 is an x-ray image of an IM nail 14 illustrating perfect circles 42 of two distal holes 15 when the C-arm is properly aligned along the ideal axis for insertion of distal screws.

Figure 10:
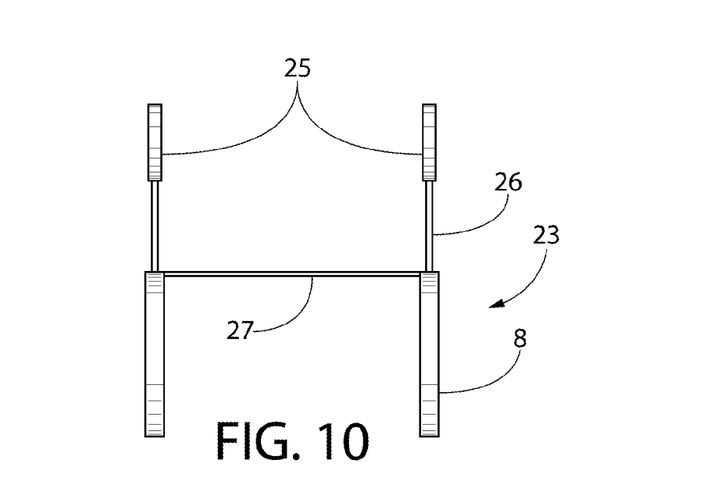
FIG. 10 is a side view of a clip on device according to the invention.

FIG. 10 is a side view of a clip on device 23 according to the invention. Radioopaque holes 25 are supported on clips 8 and cross bar 27.

Figure 11:
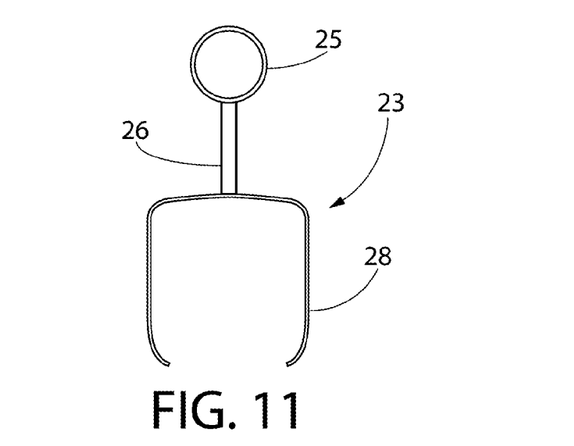
FIG. 11 is a rear view of the clip on device of FIG. 10.

FIG. 11 is a rear view of the clip on device 23 of FIG. 10.

Figure 12:
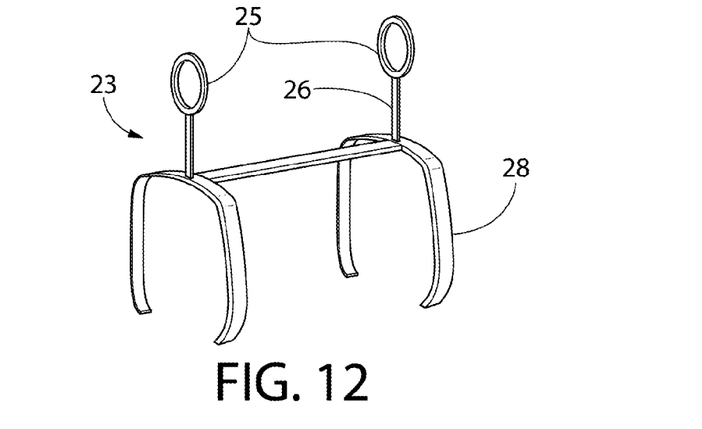
FIG. 12 is an angle view of the clip on device of FIGS. 10 and 11.

FIG. 12 is an angle view of the clip on device 23.

Figure 13:
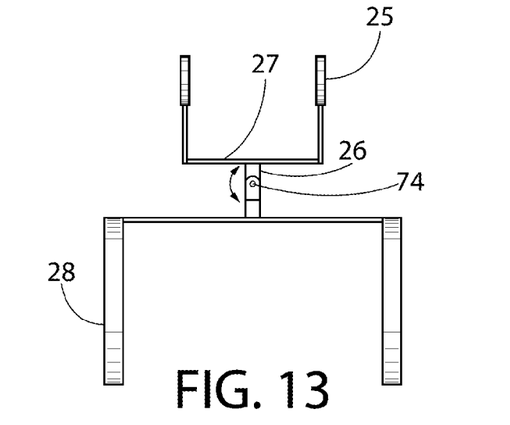
FIG. 13 is a side view of a second embodiment of a clip on device of the invention illustrating a rotatable hinge between the clip on member and the hole carrying member.

FIG. 13 is a side view of a second embodiment of a clip on device of the invention illustrating a rotatable hinge 74 between the clip on member support 27 and the hole 25 carrying member 27. In this embodiment the holes 25 can be aligned at an angle to the axis of the drill bit for drilling holes through fractured bones which do not involve an IM nail.

Figure 14:
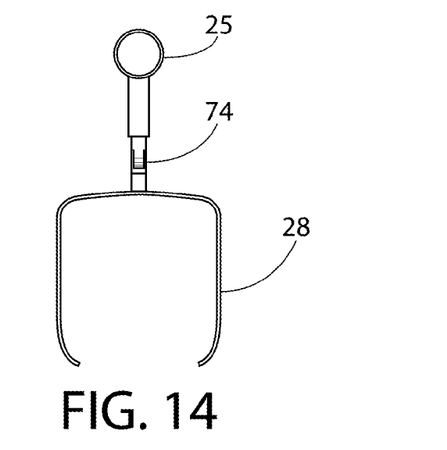
FIG. 14 is a rear view of the embodiment of FIG. 13.

FIG. 14 is a rear view of the second embodiment.

Figure 15:
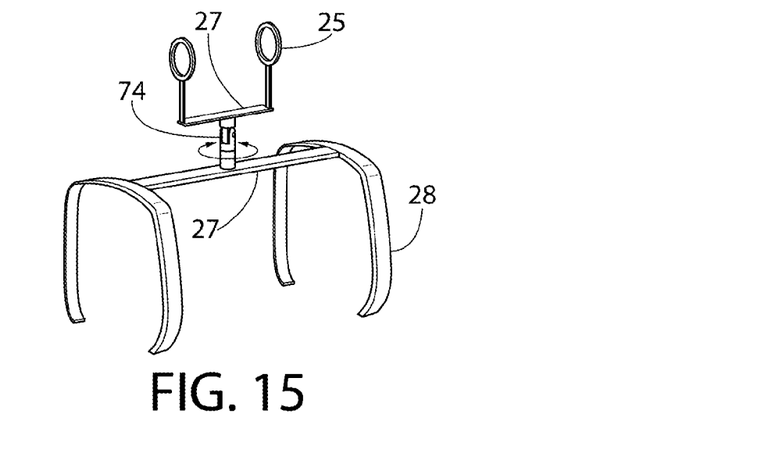
FIG. 15 is an angle view of the embodiment of FIGS. 13 and 14.

FIG. 15 is an angle view of the second embodiment.

Figure 16:
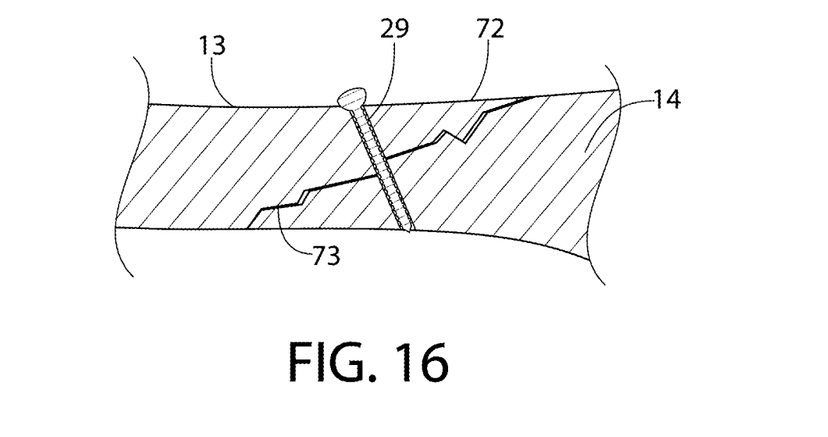
FIG. 16 is a cross-sectional view of a fractured bone with a screw properly placed in a correctly drilled hole through the two parts of the fractured bone.

The second embodiment is adapted for correctly drilling holes through bone fractures for screws to connect two parts of the bone at 90 degrees to the fracture line in situations where an IM nail is not inserted in the bone. This embodiment is for simply placing a screw by itself across a fracture line. The holes of the drill sight in this second embodiment are meant to align with the xray beam axis. In FIG. 16, for example, the fracture is aligned at about a 45 degree angle to the bone. If the bone from FIG. 16 is placed parallel to the floor on the operating room table, the surgeon would the place the C-arm so that one cylinder is directly below the patient and one cylinder is directly above the patient. This would be a vertical placement of the C-arm (opposite to the horizontal position used for the IM nail screw technique). In this orientation the C-arm axis would be perpendicular to the floor, as opposed to the prior axis for the IM nail technique where it was parallel to the floor. The modified drill sight would be set at a 45 degree angle relative to the drill. As seen in FIG. 16, once the surgeon properly aligns the drill perpendicular to the fracture line, which is at a 45 degree angle to the C-arm axis, the drill sight circles would appear as one perfect circle when an xray image is taken with the C-arm. This is not the only C-arm position or fracture orientation that this concept could be used for, but it is one example of its potential use. FIG. 16 is a cross-sectional view of a fractured bone 13 with a screw 29 properly placed in a correctly drilled hole through the two parts of the fractured bone.

Figure 17:
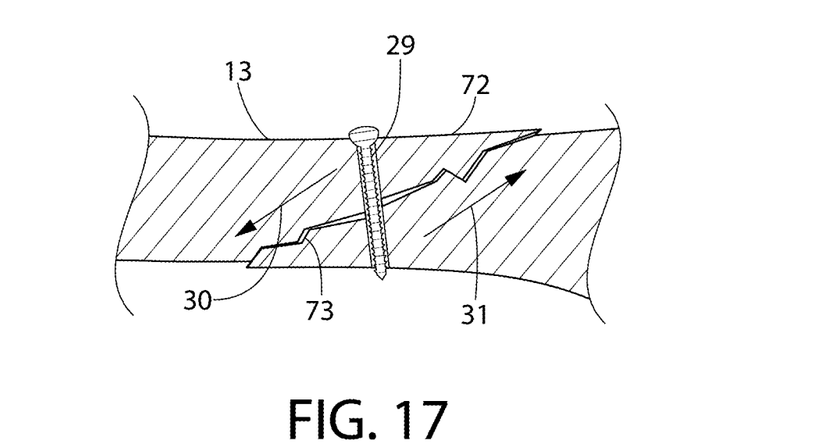
FIG. 17 is a cross-sectional view of the fractured bone of FIG. 16 with the screw improperly placed in an incorrectly drilled hole through the two parts of the fractured bone.

FIG. 17 is a cross-sectional view of the fractured bone of FIG. 16 with the screw 29 improperly placed in an incorrectly drilled hole through the two parts of the fractured bone. fractured bone 72 with a fracture line 73 oblique to the direction of the bone.

Figure 18:
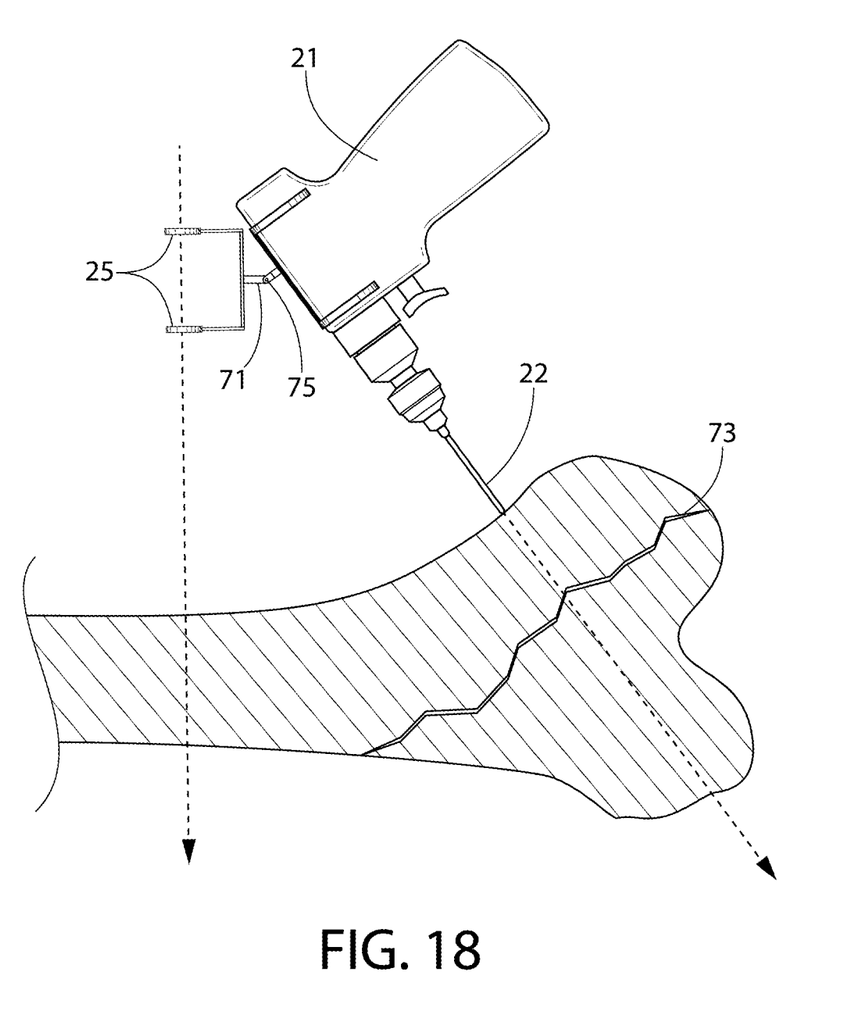
FIG. 18 is a side perspective view of a drill with the second clip on device showing the clip on device rotated so as to allow aligning of the drill at a proper angle for a particular fracture.

FIG. 18 is a side perspective view of a drill 21 with the second embodiment of the clip on device showing the clip on device rotated so as to allow aligning of the drill at a proper angle for a particular fracture. The support 71 which includes a hinge 75 rotated or adjusted in a selected offset directions versus a drill 21 on which it is mounted. The clip on device 71 of this version of the invention can be used to assist aiming the drill bit 22 perpendicular to a fracture line 73. Using this adjustable clip on device, the surgeon can use the image from the C-arm to align the circles to obtain a perfect circle in order to aim the drill bit on an axis perpendicular to the fracture line 73.

FIG. 19 is perspective view from the side of an embodiment of a drill 23, turned slightly counter-clockwise, wherein rather than a clip on device, circles are permanently mounted on the drill and can be flipped down when not in use. In this embodiment, circles 25 are hinged 74 which facilitates folding the circles 25 and their supports down (to the left in FIG. 19) and out of the way and protected from damage when the circles 25 are not needed.

The present invention, therefore, is well adapted to carry out the objects and attain the ends and advantages mentioned, as well as others inherent therein. While the invention has been depicted and described and is defined by reference to particular preferred embodiments of the invention, such references do not imply a limitation on the invention, and no such limitation is to be inferred. The invention is capable of considerable modification, alteration and equivalents in form and function, as will occur to those ordinarily skilled in the pertinent arts. The depicted and described preferred embodiments of the invention are exemplary only and are not exhaustive of the scope of the invention. Consequently, the invention is intended to be limited only by the spirit and scope of the appended claims, giving full cognizance to equivalents in all respects.

What is claimed is:

1. A method for inserting screws in holes in intramedullary (IM) nails comprising providing a surgical drill which in turn comprises a drill bit having an axis and two or more radiopaque circles on the drill, the circles having the same diameter and having planes which are parallel to each other and have an imaginary axis through them which is parallel to the axis of the drill bit, and confirming the alignment of the drill bit with the hole in the IM nail by adjusting the location and orientation of the drill to correspond to a position wherein the two or more radiopaque circles on the drill form a perfect circle in an x-ray image taken by a C-arm which has previously been aligned with a hole in the IM nail, wherein the two or more radiopaque circles are either above or on a side of the drill and can be removed or folded down on the drill when not needed; or are part of a device having a portion adapted to clip on to a top of a drill, the clip on portion being designed to correspond to the shape of the drill.

2. The method of claim 1 wherein one or more x-rays are taken to confirm the drill is aligned so that the drill bit is located on the correct axis with the intended hole in the IM nail by assuring that the external radiopaque circles on the drill form a perfect circle in an x-ray image.

3. The method of claim 1 wherein an x-ray video image of the two or more circles is displayed on a monitor so that when the image forms a perfect circle the drill bit is aligned with the intended axis.

* * * * *